US007821265B2

(12) United States Patent
Busse (10) Patent No.: US 7,821,265 B2
(45) Date of Patent: Oct. 26, 2010

(54) METHOD AND APPARATUS FOR ACQUIRING MRI DATA FOR PULSE SEQUENCES WITH MULTIPLE PHASE ENCODE DIRECTIONS AND PERIODIC SIGNAL MODULATION

(75) Inventor: Reed F. Busse, Madison, WI (US)

(73) Assignee: General Electric Co., Schenectady, NY (US)

( * ) Notice: Subject to any disclaimer, the term of this patent is extended or adjusted under 35 U.S.C. 154(b) by 265 days.

(21) Appl. No.: 12/042,099

(22) Filed: Mar. 4, 2008

(65) Prior Publication Data

US 2009/0224757 A1  Sep. 10, 2009

(51) Int. Cl.
 *G01V 3/00* (2006.01)
(52) U.S. Cl. .................................. 324/309; 324/307
(58) Field of Classification Search .............. 324/309, 324/307
 See application file for complete search history.

(56) References Cited

U.S. PATENT DOCUMENTS

| | | | | |
|---|---|---|---|---|
| 5,897,496 | A * | 4/1999 | Watanabe | 600/413 |
| 6,459,264 | B1 * | 10/2002 | Fain et al. | 324/307 |
| 7,592,809 | B1 * | 9/2009 | King et al. | 324/309 |
| 7,602,183 | B2 * | 10/2009 | Lustig et al. | 324/309 |
| 2009/0082656 | A1 | 3/2009 | Bayram et al. | |

OTHER PUBLICATIONS

Bernstein PhD et al., Effect of Windowing and Zero-Filled Reconstruction of MRI Data on Spatial Resolution and Acquisition Strategy, Journal of Magnetic Resonance Imaging 14:270-280 (2001).
Yuan et al., Three-dimensional Fast Spin-Echo Imaging: Pulse Sequence and in Vivo Image Evaluation, Journal of Magnetic Resonance Imaging 3: 894-899 (1993).
Mugler III et al., Efficient Phase-Encoding for 3D Turbo-Spin-Echo Imaging with Very Long Echo Trains, Proc. Intl. Soc. Mag. Reson. Med. 14: 2429 (2006).

* cited by examiner

*Primary Examiner*—Louis M Arana (57) ABSTRACT

A method for acquiring magnetic resonance (MR) data for a pulse sequence with periodic signal modulation and a set of views having at least two phase encode directions includes selecting a direction of modulation. Each view in the set of views is assigned a readout number based on a position of each view along the direction of modulation resulting in a plurality of readout number groups, each readout number group having a plurality of views. Each view within each readout number group is assigned a train number based on a position of each view along a second direction in k-space. MR data for the set of views is acquired based on the assigned readout number and train number for each view.

23 Claims, 6 Drawing Sheets

METHOD AND APPARATUS FOR ACQUIRING MRI DATA FOR PULSE SEQUENCES WITH MULTIPLE PHASE ENCODE DIRECTIONS AND PERIODIC SIGNAL MODULATION

TECHNICAL FIELD

The present invention relates generally to magnetic resonance imaging (MRI) systems and in particular, to a method and apparatus for view ordering to acquire MRI data for pulse sequences with multiple phase encode directions and periodic signal modulation.

BACKGROUND

Magnetic resonance imaging (MRI) is a medical imaging modality that can create images of the inside of a human body without using x-rays or other ionizing radiation. MRI uses a powerful magnet to create a strong, uniform, static magnetic field (i.e., the "main magnetic field"). When a human body, or part of a human body, is placed in the main magnetic field, the nuclear spins that are associated with the hydrogen nuclei in tissue water become polarized. This means that the magnetic moments that are associated with these spins become preferentially aligned along the direction of the main magnetic field, resulting in a small net tissue magnetization along that axis (the "z axis," by convention). A MRI system also comprises components called gradient coils that produce smaller amplitude, spatially varying magnetic fields when current is applied to them. Typically, gradient coils are designed to produce a magnetic field component that is aligned along the z axis and that varies linearly in amplitude with position along one of the x, y or z axes. The effect of a gradient coil is to create a small ramp on the magnetic field strength, and concomitantly on the resonance frequency of the nuclear spins, along a single axis. Three gradient coils with orthogonal axes are used to "spatially encode" the MR signal by creating a signature resonance frequency at each location in the body. Radio frequency (RF) coils are used to create pulses of RF energy at or near the resonance frequency of the hydrogen nuclei. These coils are used to add energy to the nuclear spin system in a controlled fashion. As the nuclear spins then relax back to their rest energy state, they give up energy in the form of an RF signal. This signal is detected by the MRI system and is transformed into an image using a computer and known reconstruction algorithms.

Magnetic resonance (MR) data may be acquired using an acquisition strategy in which multiple spatial directions are "phase-encoded," including, for example, three-dimensional (3D) acquisitions and 2D spectroscopic acquisitions. MR data is typically collected in frames that are referred to as "views." For 3D imaging, each view corresponds to a single $k_y$ and $k_z$ value, but contains data for the full range of $k_x$ values that are required to reconstruct an image. For 2D spectroscopic imaging, each view corresponds to a single $k_x$ and $k_y$ value, but contains data for the full range of chemical shift frequencies required to reconstruct a spectroscopic image. Many view-ordering techniques are known in the art for determining how $k_y$, $k_z$ or $k_x$, $k_y$ encoding is performed for each view. View ordering can be an important factor in the quality of the image produced.

Various pulse sequences have periodic signal modulation as a result of, for example, acquiring multiple lines (or "views") of k-space in a train (or shot) while magnetization is in a transient state or as a result of periodic physiologic motion. Examples of 3D pulse sequences with periodic signal modulation include RARE (Rapid Acquisition with Relaxation Enhancement) sequences (e.g., Fast Spin Echo (FSE) or Turbo Spin Echo (TSE)) that acquire multiple echoes in a train while T2-decay is occurring, fat suppression three-dimensional sequences (such as LAVA and VIBE) that execute multiple repetitions for each fat suppression pulse, inversion recovery gradient echo sequences (such as IR-SPGR (Inversion Recovery SPoiled GRadient echo) and MP-RAGE (Magnetization Prepared Rapid Gradient Echo)) that execute multiple repetitions for each inversion or preparation pulse. Three-dimensional acquisitions may also be segmented to acquire data over multiple cardiac or respiratory cycles. Periodic signal modulation can limit the practical train length (i.e., the number of readouts per train) for the acquisition, the k-space matrix size for the acquisition, and can cause blurring or ringing artifacts. Image artifacts may also be produced as a result of large jumps in k-space between acquired views that can produce erratic phase-behavior.

Various conventional view-ordering techniques have been developed for pulse sequences to produce smooth signal modulation of k-space and provide flexibility in defining train lengths. In one known technique for 3D FSE, the views are ordered such that a $k_x$-$k_y$ or $k_x$-$k_z$ plane is acquired in an integer number of echo trains. In another known technique for 3D sequences, views from multiple $k_y$-$k_z$ planes are acquired in a train by designating separate "turbo factors" for $k_y$ and $k_z$. In these techniques, however, sampling is limited to a k-space grid (or matrix) that is regular and rectangular.

To reduce the acquisition time (or scan time) for acquisitions, various methods such as parallel imaging (also known as "partially parallel imaging") and non-rectangular k-space coverage (e.g., elliptical k-space coverage) may be used. For two-dimensional (2D) accelerated parallel imaging, a non-separable auto-calibration region is most efficient. Non-rectangular k-space coverage also reduces the number of views needed to encode an image dataset. These techniques, however, are not compatible with most current view ordering techniques for sequences with multiple phase encode directions and periodic signal modulation (e.g., 3D FSE).

It would be desirable to provide a method for ordering views for pulse sequences with multiple phase encode directions and periodic signal modulation that improves scanning efficiency, maps signal modulation smoothly into k-space and enables non-rectangular k-space grids and auto-calibrating 2D accelerated parallel imaging. In addition, it would be desirable to provide a view ordering method that orders views so that the steps in k-space from one acquired view to the next are small.

BRIEF DESCRIPTION OF THE INVENTION

In accordance with an embodiment, a method for acquiring magnetic resonance (MR) data for a pulse sequence with periodic signal modulation and a set of views having at least two phase encode directions includes selecting a direction of modulation and assigning each view in the set of views a readout number based on a position of each view along the direction of modulation, the assignment resulting in a plurality of readout number groups, each readout number group having a plurality of views. The method further includes, for each readout number group, assigning each view in the plurality of views within the readout number group a train number based on a position of each view along a second direction in k-space and acquiring MR data for the set of views based at least on the assigned readout number and the assigned train number for each view.

In accordance with another embodiment, a magnetic resonance imaging (MRI) apparatus includes a magnetic resonance imaging assembly comprising a magnet, a plurality of gradient coils, at least one radio frequency coil, a radio frequency transceiver system and a pulse generator module and a controller coupled to the magnetic resonance imaging assembly and programmed to control the magnetic resonance imaging assembly to acquire magnetic resonance (MR) data using a three-dimensional (3D) pulse sequence that produces periodic signal modulation and has a set of views having at least two phase encode directions, the controller further programmed to generate a view ordering for the acquisition of the MR data by assigning each view in the set of views a readout number based on a position of each view along the direction of modulation and assigning each view in the set of views a train number based on a position of each view along a second direction in k-space.

In accordance with another embodiment, a computer readable medium having computer executable instructions for performing a method for acquiring magnetic resonance (MR) data for pulse sequences with periodic signal modulation and a set of views having at least two phase encode directions includes program code for selecting a direction of modulation, program code for assigning each view in the set of views a readout number based on a position of each view along the direction of modulation, the assignment resulting in a plurality of readout number groups, each readout number group having a plurality of views, program code for assigning each view in the plurality of views within the readout number group a train number based on a position of each view along a second direction in k-space and program code for acquiring MR data for the plurality of views based at least on the assigned readout number and the assigned train number for each view.

BRIEF DESCRIPTION OF THE DRAWINGS

Embodiments are illustrated by way of example and not limitation in the figures of the accompanying drawings, in which like reference numerals indicate corresponding, analogous or similar elements, and in which.

DETAILED DESCRIPTION

In the following detailed description, numerous specific details are set forth in order to provide a thorough understanding of embodiments. However it will be understood by those of ordinary skill in the art that the embodiments may be practiced without these specific details. In other instances, well-known methods, procedures, components and circuits have not been described in detail so as not to obscure the embodiments.

A view ordering technique or method is described herein that is compatible with three dimensional (3D) pulse sequences with periodic signal modulation as well as with two dimensional (2D) accelerated parallel imaging with a non-separable auto-calibration region and non-rectangular k-space coverage (e.g., elliptical k-space grids). Pulse sequences with multiple phase encode directions include, but are not limited to, three-dimensional (3D) acquisitions, two-dimensional (2D) spectroscopic acquisitions and other sequences where two spatial dimensions are encoded with separate readouts. In the view ordering technique, views are sorted into readouts and trains (or shots) based on their position in k-space to produce linear or radial signal modulation in k-space. Accordingly, signal modulation may be directed along an arbitrary direction in k-space (e.g., for 3D acquisitions, $k_y$, $k_z$, or $k_r$, and for spectroscopic sequences, $k_x$, $k_y$, or $k_r$). The view ordering technique increases sampling efficiency by allowing use of non-rectangular k-space coverage (e.g., elliptical k-space coverage) and 2D auto-calibrated parallel imaging, enables train lengths to be chosen independently from the k-space matrix size, maps signal modulation into k-space smoothly to limit image artifacts and limits the k-space step size between successive sampled views. The view ordering technique can be used to reduce scan time, improve resolution for a given scan time and/or provide increased control of effective TE (echo time) for FSE or T1 (inversion time) for inversion recovery (IT) sequences.

Figure 1:
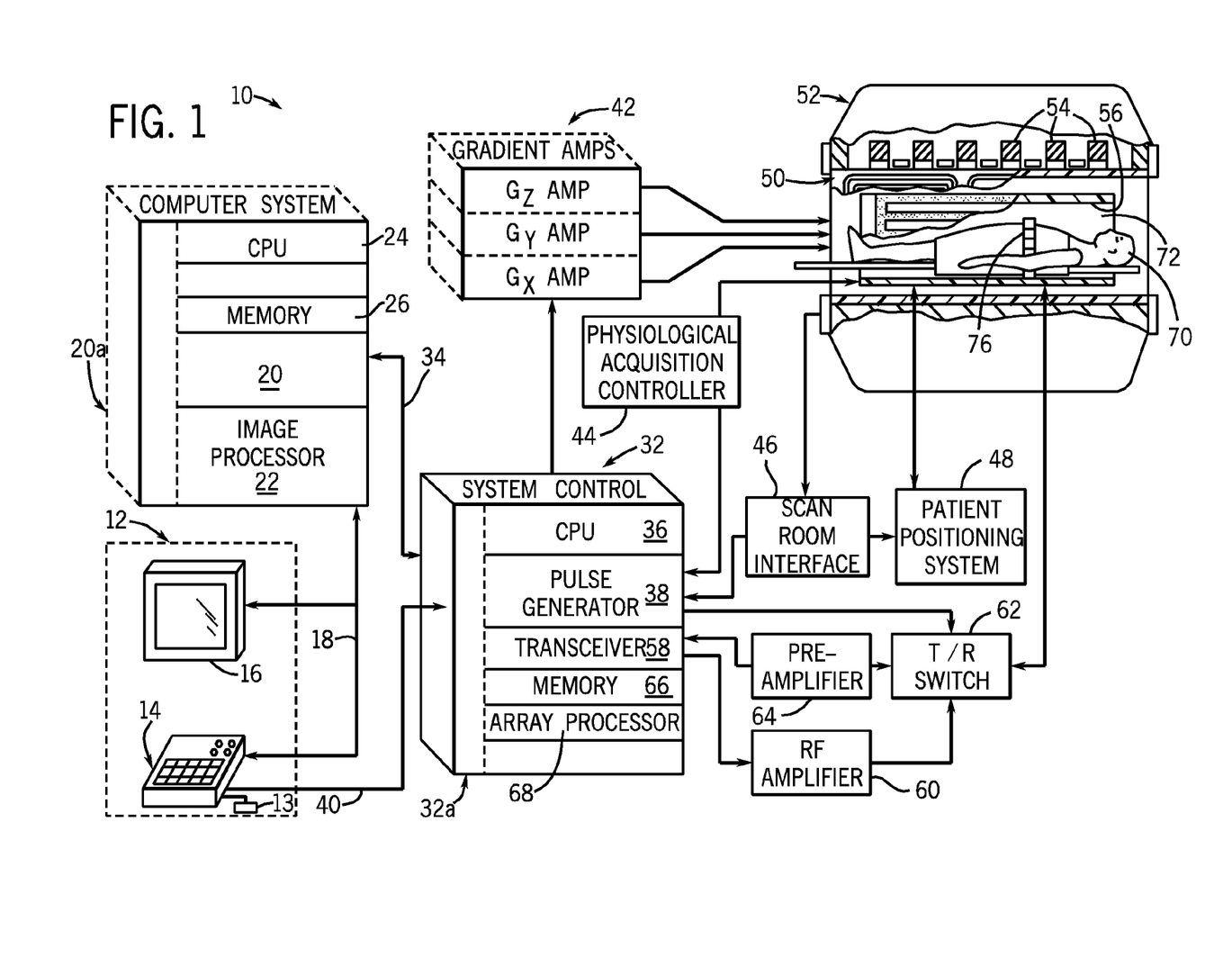
FIG. 1 is a schematic block diagram of an exemplary magnetic resonance imaging system in accordance with an embodiment.

FIG. 1 is a schematic block diagram of an exemplary magnetic resonance imaging system in accordance with an embodiment. The operation of MRI system 10 is controlled from an operator console 12 that includes a keyboard or other input device 13, a control panel 14 and a display 16. The console 12 communicates through a link 18 with a computer system 20 and provides an interface for an operator to prescribe MRI scans, display the resultant images, perform image processing on the images, and archive data and images. The computer system 20 includes a number of modules that communicate with each other through electrical and/or data connections, for example such as are provided by using a backplane 20a. Data connections may be direct wired links or may be fiber optic connections or wireless communication links or the like. The modules of computer system 20 may include an image processor module 22, a CPU module 24 and a memory module 26 that may include a frame buffer for storing image data arrays. In an alternative embodiment, the image processor module 22 may be replaced by image processing functionality on the CPU module 24. The computer system 20 is linked to archival media devices, permanent or back-up memory storage or a network. Computer system 20 may also communicate with a separate system control computer 32 through a link 34. The input device 13 can include a mouse, joystick, keyboard, track ball, touch activated screen, light wand, voice control, or any similar or equivalent input device, and may be used for interactive geometry prescription.

The system control computer 32 includes a set of modules in communication with each other via electrical and/or data connections 32a. Data connections 32a may be direct wired links, or may be fiber optic connections or wireless communication links or the like. In alternative embodiments, the modules of computer system 20 and system control computer 32 may be implemented on the same computer systems or a plurality of computer systems. The modules of system control computer 32 include a CPU module 36 and a pulse generator module 38 that connects to the operator console 12 through a communications link 40. The pulse generator module 38 may alternatively be integrated into the scanner equipment (e.g., magnet assembly 52). It is through link 40 that the system control computer 32 receives commands from the operator to indicate the scan sequence that is to be performed. The pulse generator module 38 operates the system components that play out (i.e., perform) the desired pulse sequence by sending instructions, commands and/or requests (e.g., radio frequency (RF) waveforms) describing the timing, strength and shape of the RF pulses and pulse sequences to be produced and the timing and length of the data acquisition window. The pulse generator module 38 connects to a gradient amplifier system 42 and produces data called gradient waveforms which control the timing and shape of the gradient pulses that are to be used during the scan. The pulse generator module 38 may also receive patient data from a physiological acquisition controller 44 that receives signals from a number of different sensors connected to the patient, such as ECG signals from electrodes attached to the patient. The pulse generator module 38 connects to a scan room interface circuit 46 that receives signals from various sensors associated with the condition of the patient and the magnet system. It is also through the scan room interface circuit 46 that a patient positioning system 48 receives commands to move the patient table to the desired position for the scan.

The gradient waveforms produced by the pulse generator module 38 are applied to gradient amplifier system 42 which is comprised of Gx, Gy and Gz amplifiers. Each gradient amplifier excites a corresponding physical gradient coil in a gradient coil assembly generally designated 50 to produce the magnetic field gradient pulses used for spatially encoding acquired signals. The gradient coil assembly 50 forms part of a magnet assembly 52 that includes a polarizing magnet 54 and a whole-body RF coil 56, surface or parallel imaging coils 76 or both. The coils 56, 76 may be configured for both transmitting and receiving or for transmit-only or receive-only. A patient or imaging subject 70 may be positioned within a cylindrical patient imaging volume 72 of the magnet assembly 52. A transceiver module 58 in the system control computer 32 produces pulses that are amplified by an RF amplifier 60 and coupled to the RF coils 56, 76 by a transmit/receive switch 62. The resulting signals emitted by the excited nuclei in the patient may be sensed by the same RF coil 56 and coupled through the transmit/receive switch 62 to a preamplifier 64. Alternatively, the signals emitted by the excited nuclei may be sensed by separate receive coils such as parallel or surface coils 76. The amplified MR signals are demodulated, filtered and digitized in the receiver section of the transceiver 58. The transmit/receive switch 62 is controlled by a signal from the pulse generator module 38 to electrically connect the RF amplifier 60 to the RF coil 56 during the transmit mode and to connect the preamplifier 64 to the coil during the receive mode. The transmit/receive switch 62 can also enable a separate RF coil (for example, a parallel or surface coil 76) to be used in either the transmit or receive mode.

The MR signals sensed by the RF coil 56 are digitized by the transceiver module 58 and transferred to a memory module 66 in the system control computer 32. Three dimensional (3D) MRI data is typically collected in a 3D Fourier space known in imaging as "k-space," a reciprocal space connected to real space via a Fourier transform. Typically, each MR signal, or "view," is encoded with a particular spatial frequency using "phase-encoding" and "slice-encoding" gradient pulses. For example, in a 3D Cartesian acquisition of MRI data, two directional phase encodings may be performed that correspond to a phase-encoding axis ($k_y$) and a slice-encoding axis ($k_z$). K-space is sampled by acquiring multiple phase-and slice-encoded views, each of which is defined by a unique $k_y$, $k_z$ position in the $k_y$-$k_z$ plane. Each view may acquire all the $k_x$ data for a specific pair of phase-encoding and slice-encoding values (i.e., each view may acquire all of the $k_x$ data required for its $k_y$, $k_z$ position). In another example, for a 2D spectroscopic acquisition ($k_x$, $k_y$, f), each view corresponds to a single $k_x$ and $k_y$ value, but contains data for the full range of chemical shift frequencies required to reconstruct a spectroscopic image. Multiple such digitized views are stored temporarily in the memory module 66 until they are subsequently transformed to create images. An array processor 68 uses a known transformation method, most commonly a Fourier transform, to create images from the MR signals. These images are communicated through the link 34 to the computer system 20 where it is stored in memory. In response to commands received from the operator console 12, this image data may be archived in long term storage or it may be further processed by the image processor 22 and conveyed to the operator console 12 and presented on display 16.

Figure 2:
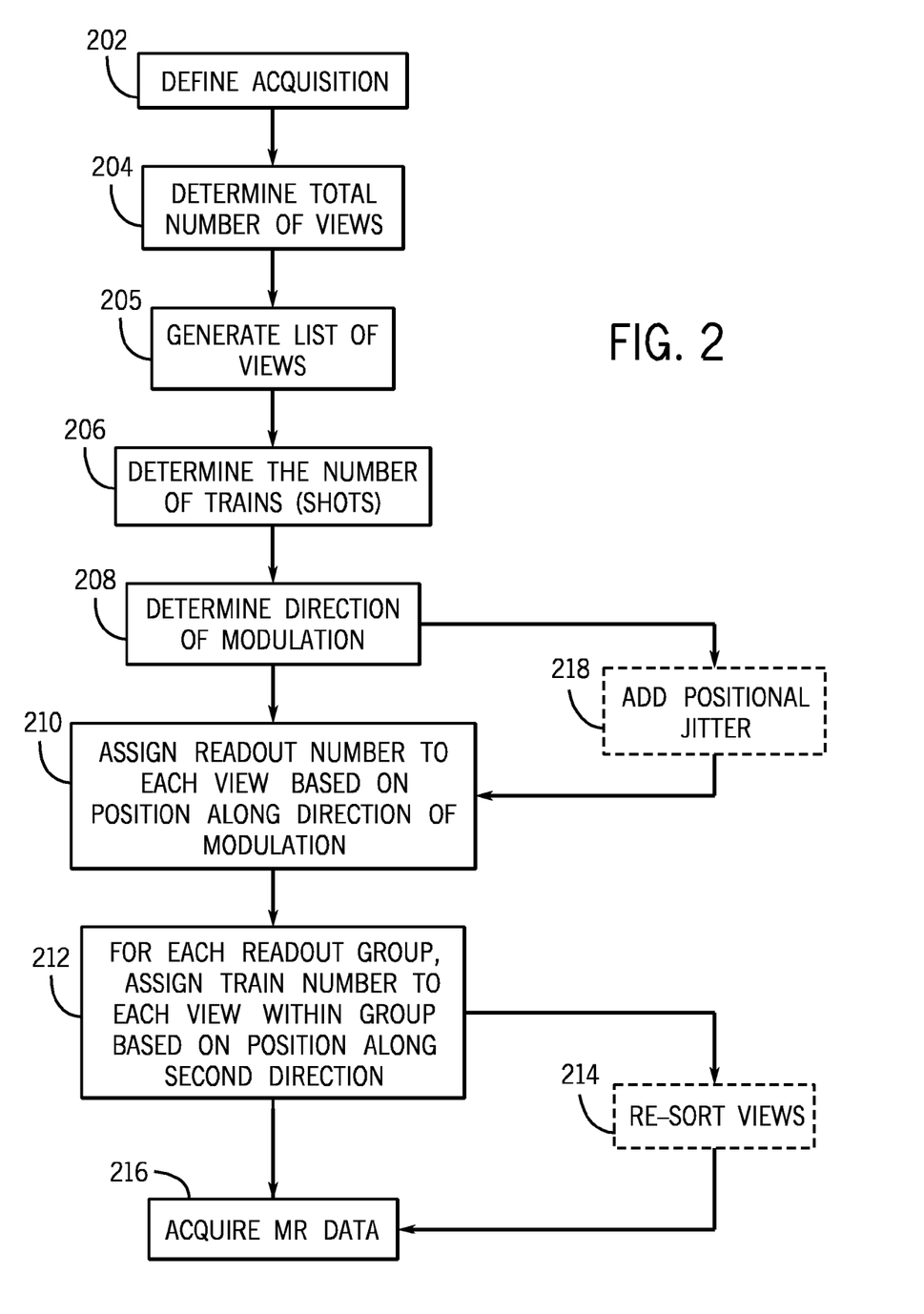
FIG. 2 is a flowchart illustrating a method for acquiring magnetic resonance (MR) data including a view ordering technique in accordance with an embodiment.

As mentioned, multiple views may be acquired using an MRI system and transformed to create images. FIG. 2 is a flowchart illustrating a method for acquiring magnetic resonance (MR) data including a view ordering technique in accordance with an embodiment. The method may be implemented using an MRI system such as described above with respect to FIG. 1 or any similar or equivalent system for obtaining MR images. For example, the view ordering technique may be part of a pulse sequence that is executed on the MRI system. At block 202, an acquisition is defined by selecting a pulse sequence and by identifying (e.g., by a user) various scan parameters, for example, field of view (FOV), matrix size, readout train length (TL) and acceleration factor. The pulse sequence is a sequence with multiple phase encode directions such as, for example, a 3D pulse sequence or a 2D spectroscopic pulse sequence. The following description of FIGS. 2-6 will be discussed with reference to a 3D pulse sequence, however, it should be understood that the view ordering technique may be used with other pulse sequences such as 2D spectroscopic sequences as mentioned above. Preferably, the pulse sequence is a pulse sequence with periodic signal modulation, e.g., a pulse sequence in which signal varies during each train (or shot) of readouts. For example, the pulse sequence may acquire multiple lines (or views) of k-space in a train during a periodic transient state of magnetization and/or periodic physiologic motion (e.g., cardiac or respiratory motion). As used herein, a train is a set of all views acquired during one signal modulation period and a readout is a sequentially ordered view within a train (e.g., the view corresponding to train N, readout M is acquired immediately before the view corresponding to train N, readout M+1).

Figure 3:
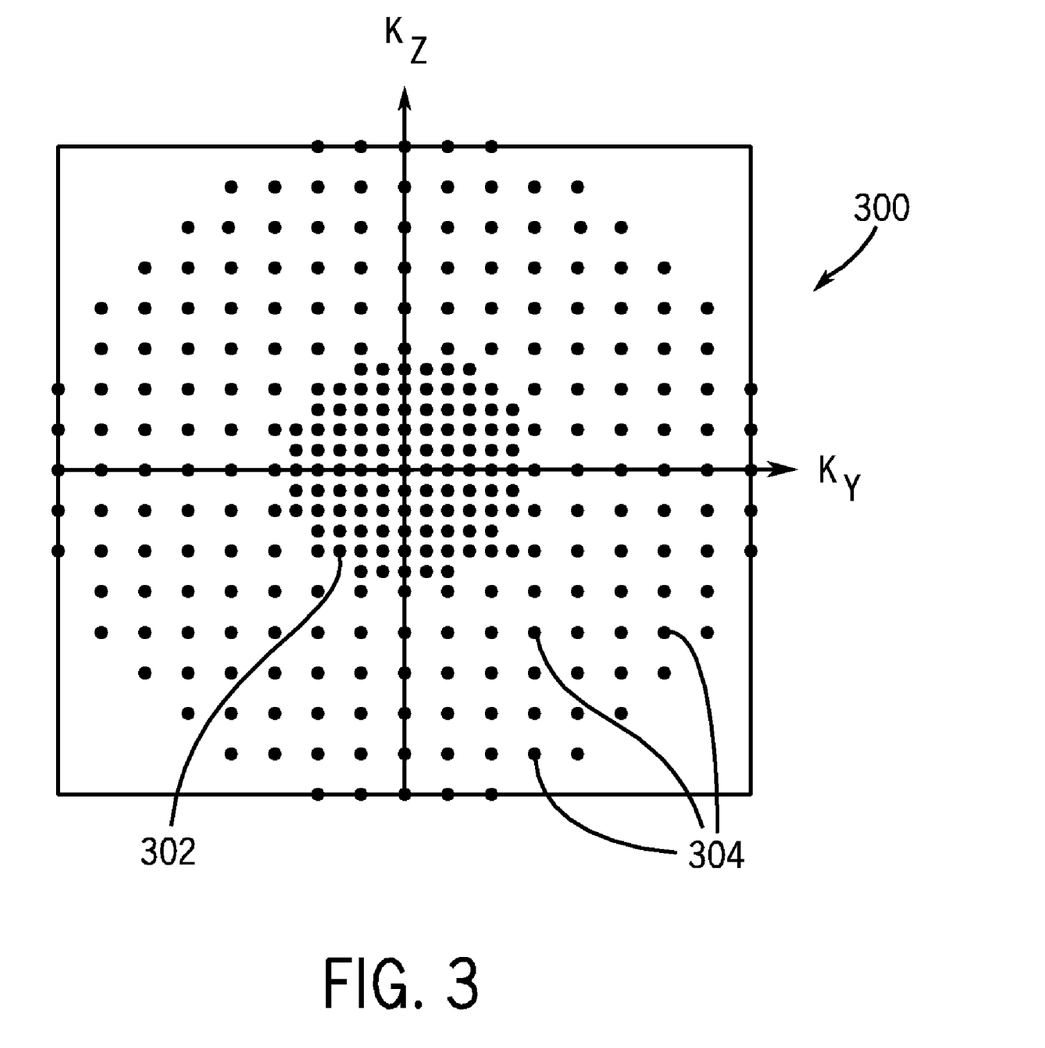
FIG. 3 is a schematic diagram showing a $k_y$-$k_z$ plane with non-rectangular k-space coverage and a non-separable auto-calibration region in accordance with an embodiment.

At block 204, a total number of views, $N_{views}$, required for the $k_y$-$k_z$ plane for the acquisition is determined. The total number of views may be determined automatically by the MRI system or input by a user. The total number of views may be determined based on various scan parameters such as matrix size. In one embodiment, where a parallel imaging technique (e.g., 2D auto-calibrated parallel imaging) is used, the total number of views is also determined based on the size of the auto-calibration region needed for parallel imaging. An exemplary $k_y$-$k_z$ plane (or grid) that is compatible with the view ordering technique described herein is shown in FIG. 3. As mentioned above, the view ordering technique enables use of non-rectangular k-space coverage and non-separable 2D auto-calibration regions. In FIG. 3, a $k_y$-$k_z$ plane (or grid) 300 is shown with elliptical k-space coverage and a non-separable 2D auto-calibration region 302. Parallel imaging and the non-rectangular k-space grid reduces the number of views acquired. The following description will discuss the view ordering technique with reference to the exemplary k-space grid shown in FIG. 3, however, it should be understood that the view ordering technique is compatible with other non-rectangular k-space grids and parallel imaging auto-calibration regions as well as with rectangular grids and to acquisitions without parallel imaging. In addition, the size of the grid 300 and the number of views 304 shown in FIG. 3 are exemplary and for illustration only.

Returning to FIG. 2, a list of all of the views to be acquired ($N_{views}$) and their k-space positions is generated at block 205. At block 206, the number of trains (or "shots"), $N_{trains}$, necessary to acquire all the views ($N_{views}$) in the $k_y$-$k_z$ grid is determined based on the number of views ($N_{views}$) and the readout train length. In one embodiment, the number of trains may be calculated using:

$$N_{trains} = \text{ceiling}\left(\frac{N_{views}}{TL}\right) \quad \text{Eqn. 1}$$

Figure 4:
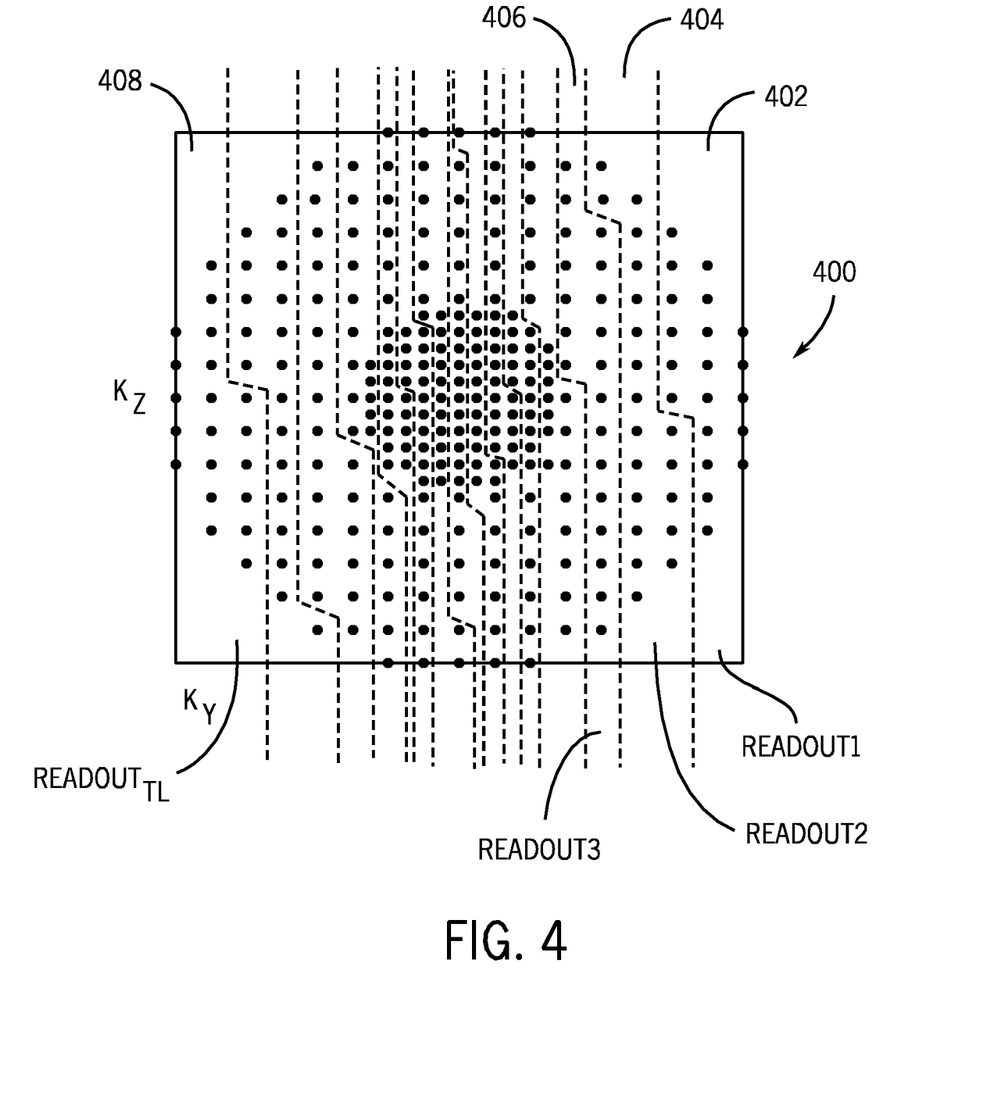
FIG. 4 is a schematic diagram showing exemplary readout assignments for views in k-space in accordance with an embodiment.
Figure 5:
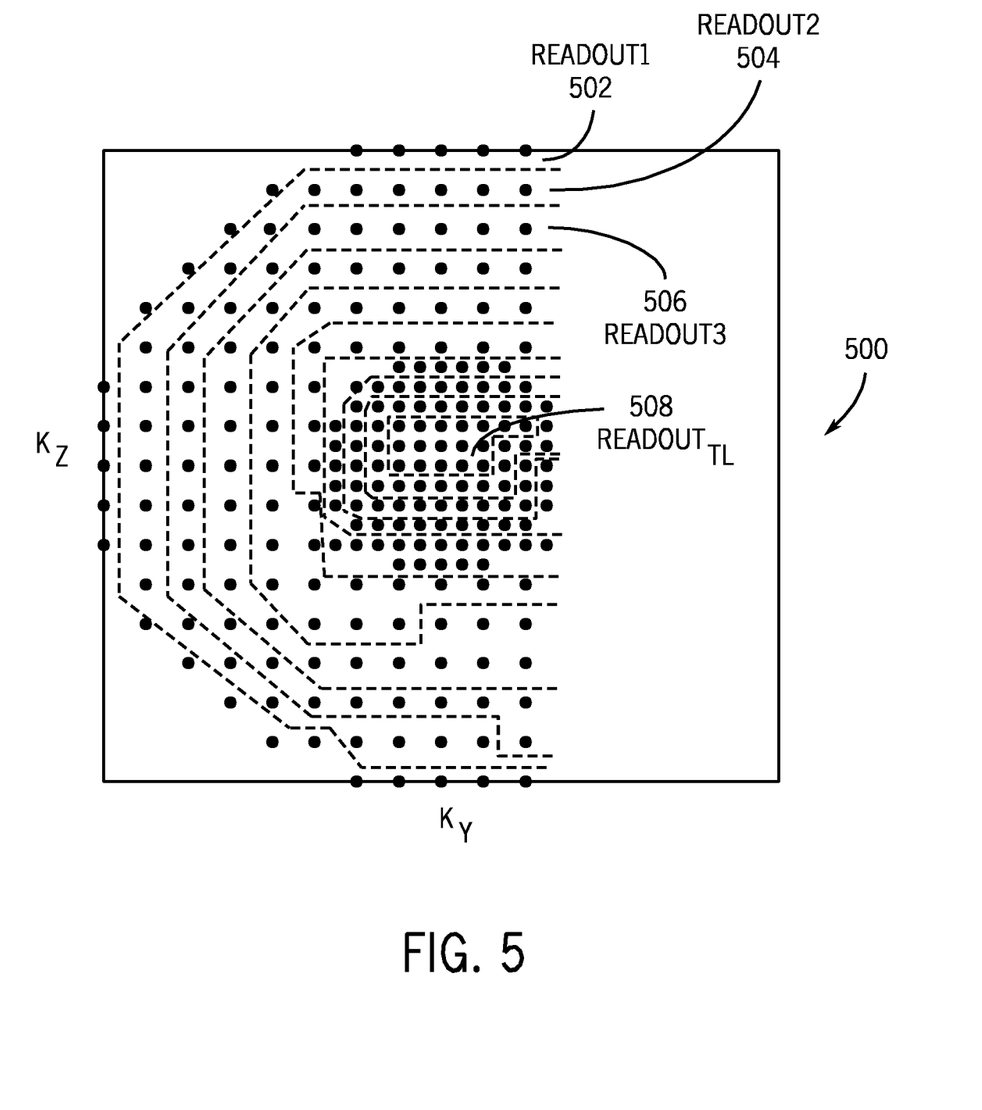
FIG. 5 is a schematic diagram showing exemplary readout assignments for views in k-space in accordance with an alternative embodiment.

At block 208, a direction of modulation is selected. In one embodiment, a direction of modulation, is chosen to produce linear modulation (e.g., $k_y$ or $k_z$). Alternatively, a direction of modulation, $k_r$, is chosen to produce radial modulation. The selection of linear or radial modulation may be based on the desired contrast. For example, linear modulation is useful for providing T2 contrast and radial modulation is useful for minimizing T2 contrast. Once a direction of modulation is selected (e.g., $k_y$, $k_z$ or $k_r$), a readout number is assigned at block 210 to each view to be acquired based on the position of the view along the chosen direction of modulation. In one embodiment, the views to be acquired are first sorted by their position along the direction of modulation. A readout number is then assigned to each view in the sorted list. For example, the first $N_{trains}$ views in the sorted list are assigned a first readout number (Readout1), the next $N_{trains}$ views are assigned a second readout number (Readout2), and so on, until the last $N_{trains}$ views are assigned a last readout number (ReadoutTL). The number of readouts (and readout groups) is defined by the train length (TL). FIG. 4 is a schematic diagram showing exemplary readout assignments for views in k-space in accordance with an embodiment. In FIG. 4, views in the $k_y$-$k_z$ plane 400 are assigned to a readout number based on their position in the $k_y$-$k_z$ plane along a direction of modulation, $k_y$. The first $N_{trains}$ views are assigned to a first readout 402 (Readout1), the next $N_{trains}$ views are assigned to a second readout 404 (Readout2), the next $N_{trains}$ views are assigned to a third readout 406 (Readout3) and so forth. The last $N_{trains}$ views in the sorted list are assigned to a last readout 408 (ReadoutTL). This results in a plurality of groups of views, each group of views assigned to a readout number from one (1) to TL. As mentioned, the selected direction of modulation may alternatively be a radial direction, $k_r$. FIG. 5 is a schematic diagram showing exemplary readout assignments for views in k-space in accordance with an alternative embodiment. In FIG. 5, views in the $k_y$-$k_z$ plane 500 are assigned to a readout based on their position in the $k_y$-$k_z$ plane along the direction of modulation, $k_r$. The first $N_{trains}$ views are assigned to a first readout 502 (Readout1), the next $N_{trains}$ views are assigned to a second readout 504 (Readout2), the next $N_{trains}$ views are assigned to a third readout 506 (Readout3) and so forth. The last $N_{trains}$ views in the sorted list are assigned to a last readout 508 (ReadoutTL). This results in a plurality of groups of views, each group of views assigned to a readout number from one (1) to TL.

Figure 6:
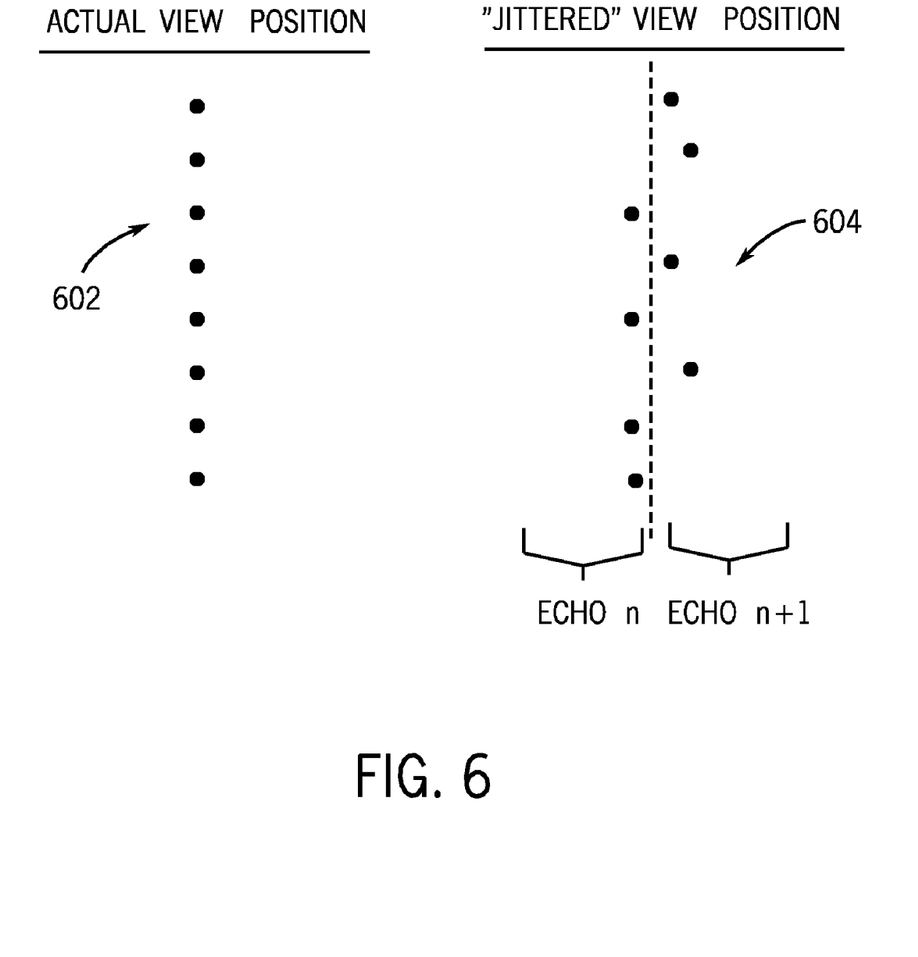
FIG. 6 shows an example of adding positional jitter to a view's k-space position in accordance with an embodiment.

Returning to FIG. 2, in another embodiment, a small amount of positional "jitter" (e.g. quasi-random or periodic) may be optionally added at block 218 to each view's k-space position (e.g., ($k_y$, $k_z$) or ($k_r$, $k_\theta$)) before assigning readout numbers and/or sorting the views. FIG. 6 shows an example of adding positional jitter to a view's k-space position in accordance with an embodiment. In column 602, an actual view position for a number of views is shown. In column 604, the "jittered" position of the views is shown. In column 604, positional jitter is added to the k-space position of each view to produce a small shift in the k-space position of each view. Adding the positional jitter to each view's k-space position disrupts the regularity of the $k_y$-$k_z$ grid and helps produce better interleaving between the trains and can also help to produce smoother signal modulation. FIGS. 4 and 5 do not illustrate the positional jitter step or the resulting interleaving for clarity.

Returning to FIG. 2, the views in each readout group (as defined by the assigned readout, e.g., Readout1, Readout 2, . . . , ReadoutTL)) are assigned a train number at block 212 based on the view's position along a second direction in k-space. The second direction is a different direction than the direction of modulation chosen at block 208, for example, in one embodiment, the second direction is orthogonal to the direction of modulation. For example, if the selected direction of modulation is $k_y$, the second direction may be $k_z$. Alternatively, if the selected direction of modulation is $k_r$, the second direction may be $k_\theta$. For each readout group, a train number (i.e., from one (1) to $N_{trains}$) is assigned to each view within the readout group. In one embodiment, the views within a readout group are first sorted by their position along the second direction in k-space. A train number is then assigned to each view within the readout group. For example, the first view in the group is assigned to a first train, the second view in the group is assigned to a second train, and so on until the last view in the group is assigned to the last train. The result of the view ordering is that each view is assigned a readout number and a train number for the acquisition based on the view's position along the selected direction of modulation and along the second direction, respectively.

Before MR data is acquired at block 216, additional, optional re-sorting may be performed at block 214 to, for example, further reduce the step size in k-space from readout to readout. For example, in one embodiment, for each train number, the views assigned to the particular train may be resorted by position along the second direction in k-space. In addition, the views assigned to the particular train may be resorted by position along the direction of modulation. In another embodiment, the views may be resorted to implement a full cycle of modulation, amendable to "scrolling" the effective TE, as is known in the art for 2D FSE sequences.

Once the view ordering is determined, MR data may be acquired at block 216 by an MRI system in accordance with at least the selected pulse sequence, the view ordering and the scan parameters. The actual k-space position of each view is used for data acquisition rather than the "jittered" position that may be used for assigning readout and train numbers to the views and sorting the views as described above with respect to block 218 in FIG. 2. Once the MR data is acquired, it may be stored in memory and used to reconstruct an image or images using known image reconstruction techniques.

In one embodiment, the desired contrast for a scan may be attained by coordinating the acquisition of the center of k-space with that portion of a train that has the desirable contrast. In another embodiment, sensitivity to motion may be decreased by coordinating the acquisition of the center of k-space with that portion of a train that coincides with the least motion.

As mentioned above, the view ordering technique described herein is compatible with pulse sequences with multiple phase encode directions and periodic signal modulation. Such pulse sequences include, but are not limited to, 2D spectroscopic sequences, RARE sequences (e.g., FSE, TSE), fat suppression sequences such as LAVA and VIBE, inversion recovery gradient echo sequences such as MP-RAGE and IR-SPGR, other sequences utilizing preparation pulses, and acquisitions segmented to acquire data over multiple cardiac or respiratory cycles. In addition, the view ordering technique is compatible with rectangular and non-rectangular k-space grids, parallel imaging with separable or non-separable auto-calibration regions or without separable or non-separable auto-calibration regions and acquisitions without parallel imaging.

Computer-executable instructions for determining a view-ordering for a 3D acquisition with periodic signal modulation according to the above-described method may be stored on a form of computer readable media. Computer readable media includes volatile and nonvolatile, removable and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which can be used to store the desired instructions and which may be accessed by MRI system 10 (shown in FIG. 1), including by internet or other computer network forms of access.

A technical effect of the disclosed method and apparatus is that it provides for acquisition of MR data using a pulse sequence with multiple phase encode directions and periodic signal modulation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the present invention without departing from the spirit thereof. The scope of these and other changes will become apparent from the appended claims.

I claim:

1. A method for acquiring magnetic resonance (MR) data for a pulse sequence with periodic signal modulation and a set of views having at least two phase encode directions, the method comprising:
    selecting a direction of modulation;
    assigning each view in the set of views a readout number based on a position of each view along the direction of modulation, the assignment resulting in a plurality of readout number groups, each readout number group having a plurality of views;
    for each readout number group, assigning each view in the plurality of views within the readout number group a train number based on a position of each view along a second direction in k-space; and
    acquiring MR data for the set of views based at least on the assigned readout number and the assigned train number for each view.

2. A method according to claim 1, wherein assigning each view in the set of views a readout number based on a position of each view along the direction of modulation comprises sorting the set of views based on position along the direction of modulation before assigning each view a readout number.

3. A method according to claim 1, wherein assigning each view in the plurality of views within the readout number group a train number based on a position of each view along a second direction in k-space comprises sorting the plurality of views within the readout number group based on position along the second direction before assigning each view in the readout number group a train number.

4. A method according to claim 1, wherein the set of views defines a non-rectangular k-space grid.

5. A method according to claim 1, wherein the set of views defines a k-space grid including a non-separable auto-calibration region.

6. A method according to claim 1, further comprising before acquiring MR data, resorting views associated with at least one train.

7. A method according to claim 6, wherein resorting views associated with at least one train comprises sorting the views by position along the second direction.

8. A method according to claim 7, wherein resorting views associated with at least one train further comprises sorting the views by position along the direction of modulation.

9. A method according to claim 1, wherein the direction of modulation is selected to generate linear modulation.

10. A method according to claim 9, wherein the direction of modulation is selected to generate radial modulation.

11. A magnetic resonance imaging (MRI) apparatus comprising:
    a magnetic resonance imaging assembly comprising a magnet, a plurality of gradient coils, at least one radio frequency coil, a radio frequency transceiver system and a pulse generator module; and
    a controller coupled to the magnetic resonance imaging assembly and programmed to control the magnetic resonance imaging assembly to acquire magnetic resonance (MR) data using a three-dimensional (3D) pulse sequence that produces periodic signal modulation and has a set of views having at least two phase encode directions, the controller further programmed to generate a view ordering for the acquisition of the MR data by assigning each view in the set of views a readout number based on a position of each view along the direction of modulation and assigning each view in the set of views a train number based on a position of each view along a second direction in k-space.

12. An MRI apparatus according to claim 11, wherein assigning each view in the set of views a readout number comprises sorting the set of views based on position along the direction of modulation.

13. An MRI apparatus according to claim 11, wherein assigning each view to a readout number results in a plurality of readout number groups, each readout number group having a plurality of views.

14. An MRI apparatus according to claim 13, wherein assigning each view in the set of views a train number comprises sorting the plurality of views within each readout number group by position along the second direction and for each readout number group, assigning each view within the readout number group to a train.

15. An MRI apparatus according to claim 11, wherein the direction of modulation generates linear modulation.

16. An MRI apparatus according to claim 11, wherein the direction of modulation generates radial modulation.

17. A non-transitory computer readable medium having computer executable instructions for performing a method for acquiring magnetic resonance (MR) data for pulse sequences with periodic signal modulation and a set of views having at least two phase encode directions, the computer readable medium comprising:
   program code for selecting a direction of modulation;
   program code for assigning each view in the set of views a readout number based on a position of each view along the direction of modulation, the assignment resulting in a plurality of readout number groups, each readout number group having a plurality of views;
   program code for assigning each view in the plurality of views within the readout number group a train number based on a position of each view along a second direction in k-space; and
   program code for acquiring MR data for the plurality of views based at least on the assigned readout number and the assigned train number for each view.

18. A non-transitory computer readable medium according to claim 17, wherein the program code for assigning each view in the set of views a readout number based on a position of each view along the direction of modulation comprises program code for sorting the set of views based on position along the direction of modulation before assigning each view a readout number.

19. A non-transitory computer readable medium according to claim 17, wherein the program code for assigning each view in the plurality of views within the readout number group a train number based on a position of each view along a second direction in k-space comprises program code for sorting the plurality of views within the readout number group based on position along the second direction before assigning each view in the readout number group a train number.

20. A non-transitory computer readable medium according to claim 17, wherein the set of views defines a non-rectangular k-space grid.

21. A non-transitory computer readable medium according to claim 17, wherein the set of views defines a k-space grid including a non-separable auto-calibration region.

22. A non-transitory computer readable medium according to claim 17, wherein the direction of modulation is selected to generate linear modulation.

23. A non-transitory computer readable medium according to claim 17, wherein the direction of modulation is selected to generate radial modulation.

* * * * *